(12) United States Patent
Chandrashekaran et al.

(10) Patent No.: US 9,580,488 B2
(45) Date of Patent: Feb. 28, 2017

(54) FUSION TAGS AND EXPRESSION VECTOR SYSTEM FOR THE EXPRESSION OF HUMAN PARATHYROID HORMONE (RHPTH)

(71) Applicants: Siddamadappa Chandrashekaran, Bangalore (IN); Venkat Hemalatha, Bangalore (IN)

(72) Inventors: Siddamadappa Chandrashekaran, Bangalore (IN); Venkat Hemalatha, Bangalore (IN)

(*) Notice: Subject to any disclaimer, the term of this patent is extended or adjusted under 35 U.S.C. 154(b) by 0 days.

(21) Appl. No.: 14/653,897

(22) PCT Filed: Dec. 23, 2013

(86) PCT No.: PCT/IN2013/000792
§ 371 (c)(1),
(2) Date: Jun. 19, 2015

(87) PCT Pub. No.: WO2014/097323
PCT Pub. Date: Jun. 26, 2014

(65) Prior Publication Data
US 2016/0009779 A1    Jan. 14, 2016

(30) Foreign Application Priority Data
Dec. 21, 2012 (IN) .......................... 3579/MUM/2012

(51) Int. Cl.
| | | |
|---|---|---|
| *C12P 21/04* | (2006.01) | |
| *C12P 21/06* | (2006.01) | |
| *C12N 15/00* | (2006.01) | |
| *C07H 21/02* | (2006.01) | |
| *C07H 21/04* | (2006.01) | |
| *C07K 14/635* | (2006.01) | |
| *C07K 14/245* | (2006.01) | |

(52) U.S. Cl.
CPC .......... *C07K 14/635* (2013.01); *C07K 14/245* (2013.01); *C07K 2319/50* (2013.01)

(58) Field of Classification Search
None
See application file for complete search history.

(56) References Cited

U.S. PATENT DOCUMENTS

| | | | | |
|---|---|---|---|---|
| 5,270,181 A | * | 12/1993 | McCoy | C07K 14/00 435/243 |
| 7,618,799 B2 | * | 11/2009 | Coleman | C12N 15/625 435/183 |
| 7,630,836 B2 | * | 12/2009 | Omura | C12Q 1/689 702/19 |
| 7,655,413 B2 | * | 2/2010 | Butt | C07K 14/00 435/7.1 |
| 2003/0134352 A1 | | 7/2003 | Freimuth et al. | |
| 2010/0145033 A1 | | 6/2010 | Sankararaman | |
| 2011/0252501 A1 | * | 10/2011 | Abad | C12N 15/8261 800/275 |

OTHER PUBLICATIONS

Smialowski, Doose, Torkler, Kaufman, and Frishman, "Proso II—a new method for protein solubility prediction", The FEBS Journal, Apr. 12, 2012, pp. 2192-2200, vol. 279, issue 12, Wiley on behalf of the Federation of European Biochemical Societies. (http://onlinelibrary.wiley.com/doi/10.1111/j.1742-4658.2012.08603.x/full).

Green and Sambrook, "Molecular Cloning: A Laboratory Manual" 4th edition, 2012, Cold Spring Harbor Laboratory Press, Cold Spring Harbor, New York, USA.

* cited by examiner

*Primary Examiner* — Shulamith H Shafer
(74) *Attorney, Agent, or Firm* — George W. Moxon, II; Brian Harrod

(57) ABSTRACT

The present invention provides for fusion tags of 20 to 40 amino acids having a sequence as given in FIG. 1, fusion tags sharing homology with these fusion tags, or hybrid fusion tags comprising sequences of FIG. 1. The invention further provides an expression vector system comprising a fusion tag of the invention, and a process of obtaining recombinant human parathyroid hormone by using the fusion tags and the expression vector system of the invention.

14 Claims, 8 Drawing Sheets

FIG. 1
Tag 1: DSLRFLYDGIRIQADQAPEDLDMELGS (SEQ ID NO:1)
Tag 2: GSDSEVNQEAKPEVKPEVKLGS (SEQ ID NO:2)
Tag 3: GNQDEDFATVLVEEAKPEVKPEVKLGS (SEQ ID NO:3)
Tag 4: EFTLTGLGQVIIGGGPAGLRTEEGFLVRGLFSHVVTEIL (SEQ ID NO:4)
Tag 5: ENYPGFPEGISGPEAGREAKQAEKFGARIVMDEVQGEGS (SEQ ID NO:5)
Tag 6: GKLTVAKLNIDQNPGTAPKYGIRGIPTTKVGALSKGQLGS (SEQ ID NO:6)
Tag 7: MSDKIIHLTDDSFDTDVLKADGAILVDFWAEWGPKGS (SEQ ID NO:7)

FIG. 2

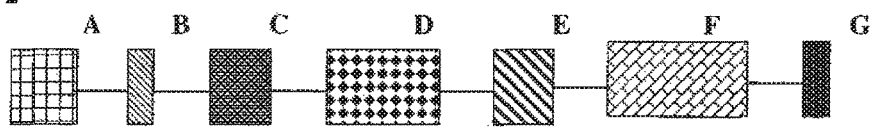

Fusion protein

FUSION TAGS AND EXPRESSION VECTOR SYSTEM FOR THE EXPRESSION OF HUMAN PARATHYROID HORMONE (RHPTH)

This application claims priority benefit of Indian provisional patent application No. 3579/MUM/2012, filed Dec. 21, 2012, incorporated fully herein by reference.

FIELD OF THE INVENTION

The present invention relates to novel fusion tags and use of these tags to create a novel vector system for efficient expression of recombinant proteins.

BACKGROUND

Protein expression systems are used widely to produce desired proteins in biotechnology and more recently to produce sets (combinatorial series) of proteins that are screened for drug discovery purposes. Even though commonly used protein expression systems include those derived from bacteria, yeast, baculovirus/insect and mammalian cells etc., *E. coli* remains a preferred choice for researchers expressing therapeutic proteins and peptides. There are potential limitations in gene expression in *E. coli*, however, including toxicity of the foreign peptide, protein insolubility, protease degradation of smaller peptides, improper folding, and inappropriate posttranslational modifications.

The expression of small peptides such as recombinant human parathyroid hormone (rhPTH) in *E. coli* has remained challenging because of low expression levels. Recombinant fusion expression systems, such as glutathione-S-transferase (GST), thioredoxin (Trx), Sumo, Nus, Intein, and chitin are available for production of small peptides/proteins in the range of 30 to 100 amino acids. Proteins expressed using these available expression systems may be soluble, but the final yields of the protein are often compromised due to the larger size of the fusion partner.

Further regarding parathyroid hormone (PTH, parathormone or parathyrin) is an 84-amino acid polypeptide secreted by the parathyroid gland. This hormone is secreted from cells of the parathyroid glands and finds its major target cells in bone and kidney. Like most other protein hormones, parathyroid hormone is synthesized as a preprophormone. After intracellular processing, the mature hormone is packaged within the Golgi into secretory vesicles, the secreted into blood by exocytosis. It acts to increase the concentration of calcium in the blood by acting upon the parathyroid hormone 1 receptor and the parathyroid hormone 2 receptor.

Recombinant Human Parathyroid hormone (e.g., rhPTH [1-84], or the smaller rhPTH[1-34] or rhPTH[1-31] peptides) is indicated therapeutically for use in postmenopausal women with osteoporosis at a high risk for fracture or with a history of osteoporotic fracture, patients with multiple risk factors for fracture, and for patients who have failed or are intolerant to other available osteoporosis therapy. Additionally, rhPTH is indicated to increase bone mass in men with primary or hypogonadal osteoporosis at high risk of fracture, patients with multiple risk factors for fracture, and for patients who have failed or are intolerant to other available osteoporosis therapy. rhPTH is also indicated for the treatment of men and women with osteoporosis associated with sustained systemic glucocorticoid therapy. Thus, there are important medical needs for improved approaches in producing rhPTH.

SUMMARY OF THE INVENTION

The embodiments of the present invention provide for novel fusion tags, expression vector systems comprising the novel fusion tags, and processes of obtaining parathyroid hormone, for example rhPTH(1-34), using these novel fusion tags.

More specifically, aspects of the present invention provide fusion tags of 20 to 40 amino acids, such as DSLRFLYD-GIRIQADQAPEDLDMELGS (SEQ ID NO:1), GSD-SEVNQEAKPEVKPEVKLGS (SEQ ID NO:2), GNQDED-FATVLVEEAKPEVKPEVKLGS (SEQ ID NO:3), EFTLTGLGQVIIGGGPAGLRTEEGFLVRGLFSHV-VTEIL (SEQ ID NO:4), ENYPGFPEGISGPEA-GREAKQAEKFGARIVMDEVQGEGS (SEQ ID NO:5), GKLTVAKLNIDQNPGTAPKYGIRGIPTTKVGALSK-GQLGS (SEQ ID NO:6), MSDKIIHLTDDSFDTDV-LKADGAILVDFWAEWGPKGS (SEQ ID NO:7), fusion tags homologous with these, or hybrid tags created using the amino acid sequences of these tags.

Further aspects of the invention provide polynucleotides that encode these novel fusion tags, and expression vector systems comprising these fusion tags and rhPTH. In particular embodiments, the fusion tags are fused with His-tag, followed by TEV cleavage site and rhPTH, in a vector backbone.

Other aspects of the invention provide for processes of obtaining rhPTH by using these fusion tags, comprising, for example, chemical synthesis of a polynucleotide that encodes a fusion protein comprising a novel fusion tag and rhPTH, cloning the polynucleotide into a vector backbone, expressing the fusion protein in *E. coli* cells in insoluble form, obtaining the rhPTH from the fusion protein, and partially purifying the rhPTH.

DESCRIPTIONS OF THE DRAWINGS

FIG. 1 presents the amino acid sequence of particular example fusion tags.

FIG. 2 shows a schematic representation of a recombinant genetic construct containing a novel tag. The letters indicate the following genetic blocks: A: Promoter, B: Start Codon, C: His Tag, D: Peptide Tag, E: TEV cleavage site, F: rhPTH, G: Stop.

Figure 4:
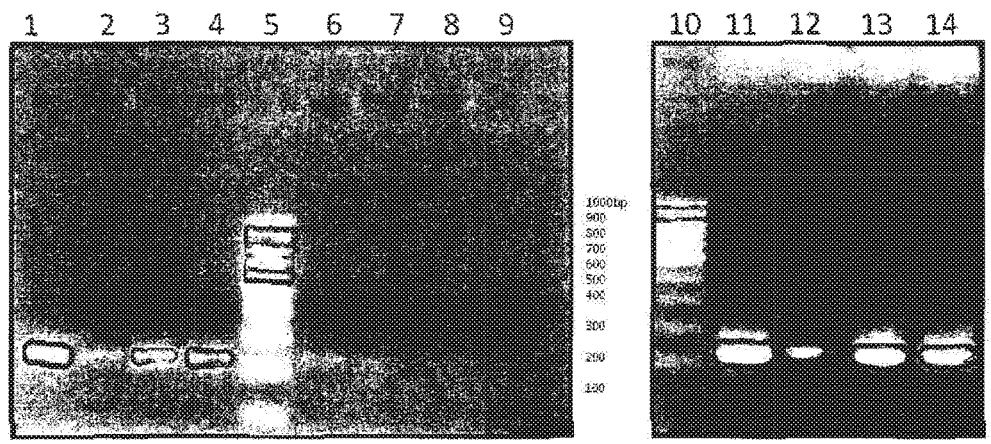

FIG. 4 presents photographs of gels showing the amplification of several tags, TagPTH (tags 1-3). Lanes 1-4: PCR products of TagPTH1; Lanes 5 and 10: 100 bp DNA ladder (marker); Lanes 6-9: PCR products of TagPTH2; Lanes 11-14: PCR products of TagPTH3.

Figure 5:
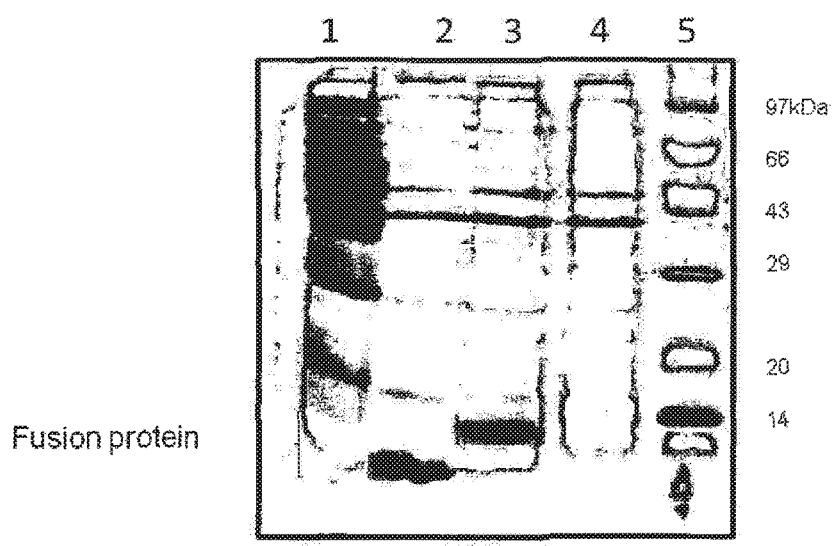

FIG. 5 depicts results of a 15% SDS polyacrylamide gel analysis for fusion protein expression (bracket) from each of the plasmids. Lane 1: uninduced BL21DE3 TagPTH1 cell lysate; Lane 2: induced BL21DE3 TagPTH1 cell lysate; Lane 3: induced BL21DE3 TagPTH2 cell lysate; Lane 4: induced BL21DE3 TagPTH3 cell lysate; Lane 5: Molecular weight marker.

Figure 6:
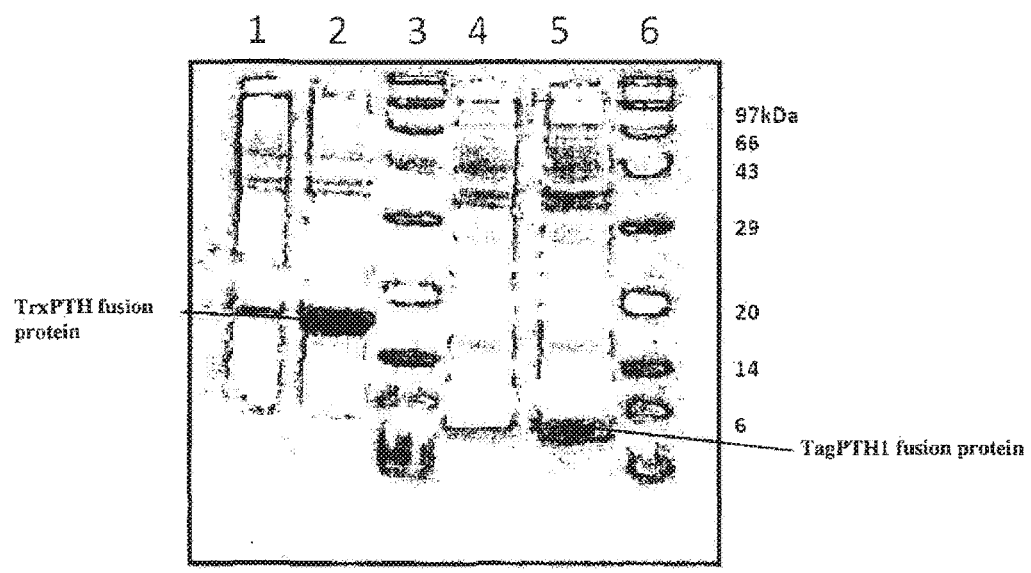

FIG. 6 depicts results of a 15% SDS polyacrylamide gel analysis for fusion protein expression (bracket) from TrxPTH and TagPTH1. Lane 1: uninduced BL21DE3 TrxPTH cell lysate; Lane 2: induced BL21DE3 TrxPTH cell lysate; Lanes 3 and 6: Molecular weight marker. Lane 4: uninduced BL21DE3 TagPTH1 cell lysate; Lane 5: induced BL21DE3 TagPTH1 cell lysate.

Figure 7:
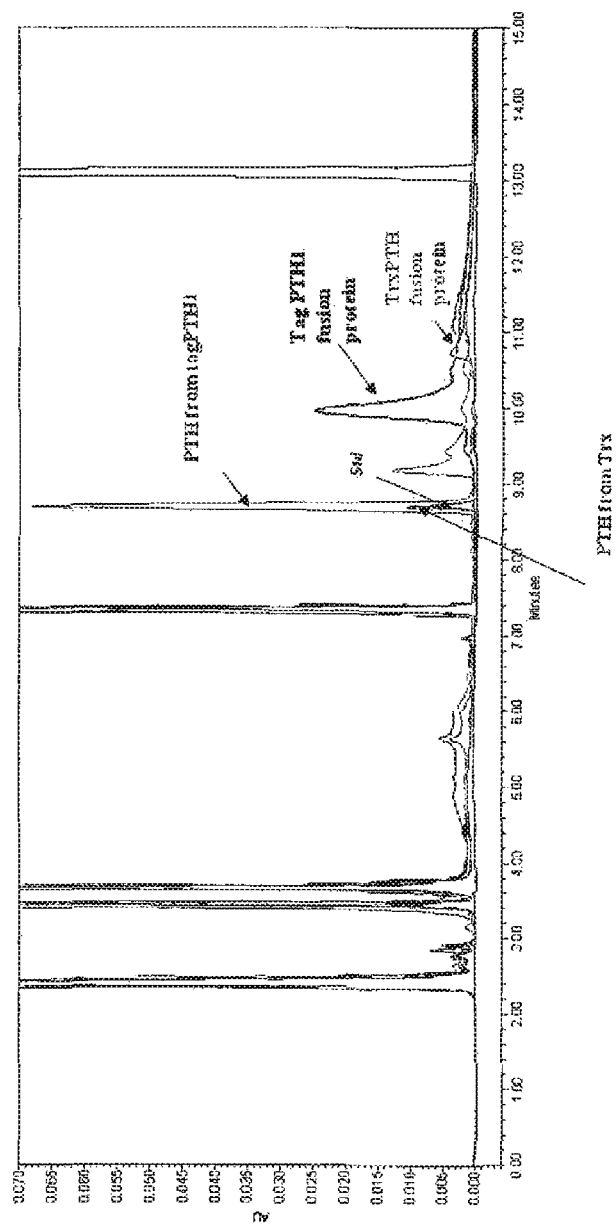

FIG. 7 presents a TrxPTH and Tag PTH1 Fusion protein and cleavage profile in RP-HPLC.

Figure 8:
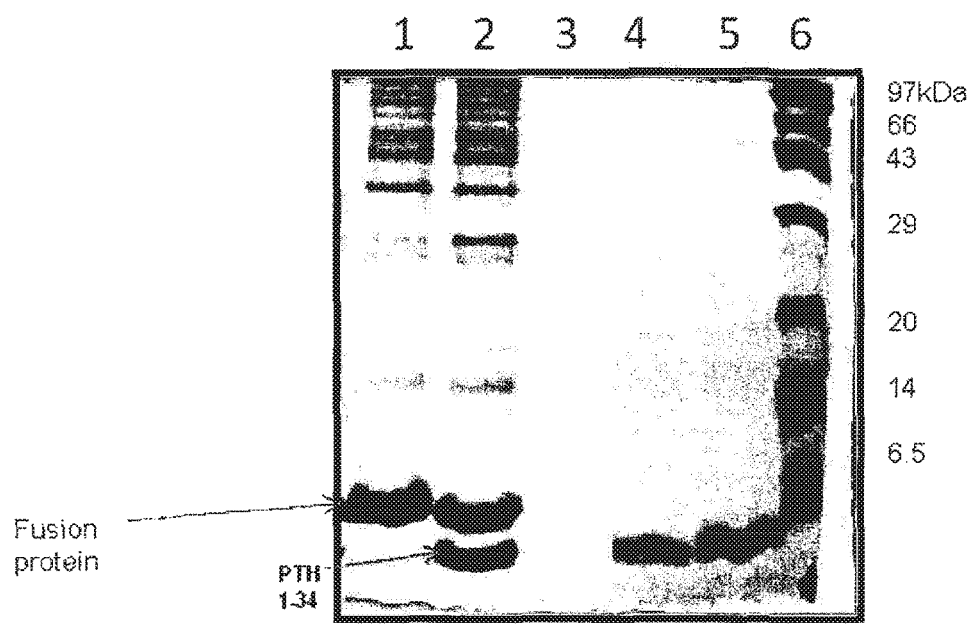

FIG. 8 shows results of a 15% SDS polyacrylamide gel analysis for TagPTH1 expression and protease cleavage. Lane 1: undigested TagPTH1 fusion protein (arrow); Lane 2: TEV protease-digested Tag PTH1 protein (PTH arrow); Lanes 3-5: different fractions of digested TagPTH1 from a PD10 column; Lane 6: molecular weight marker.

Figure 9A:
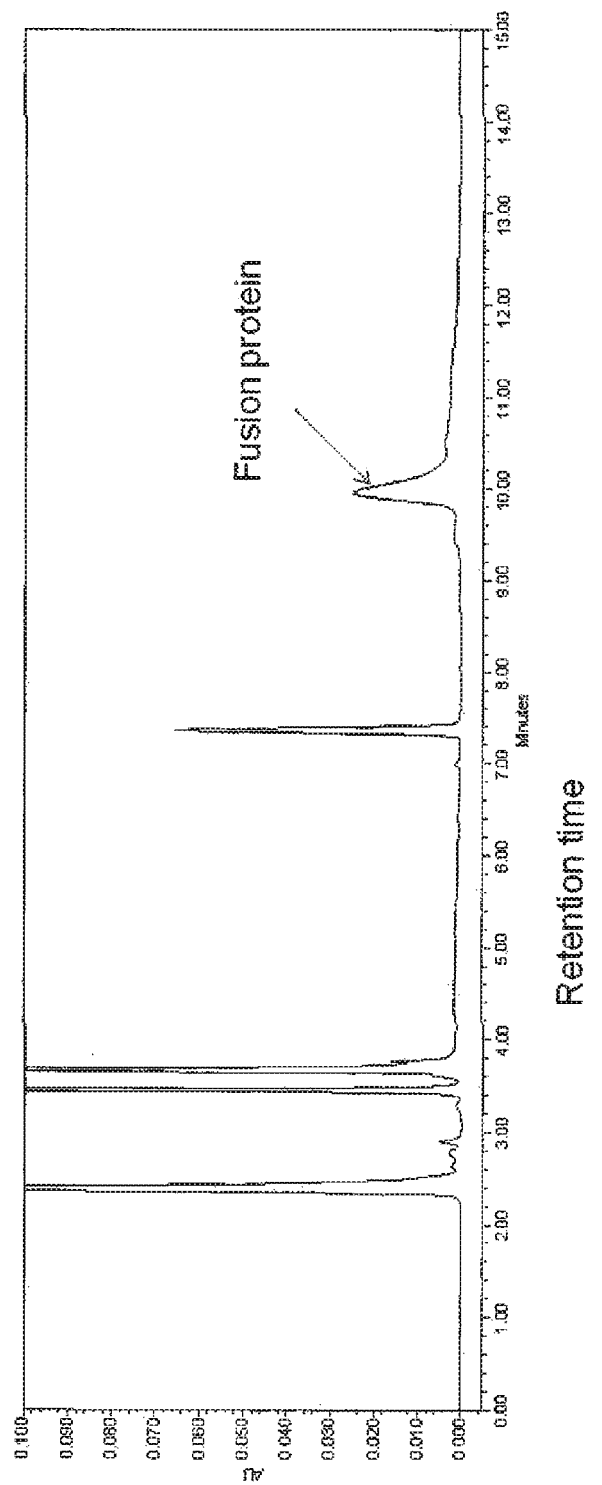

FIG. 9a presents a TagPTH1 Fusion protein profile in RP-HPLC.

Figure 9B:
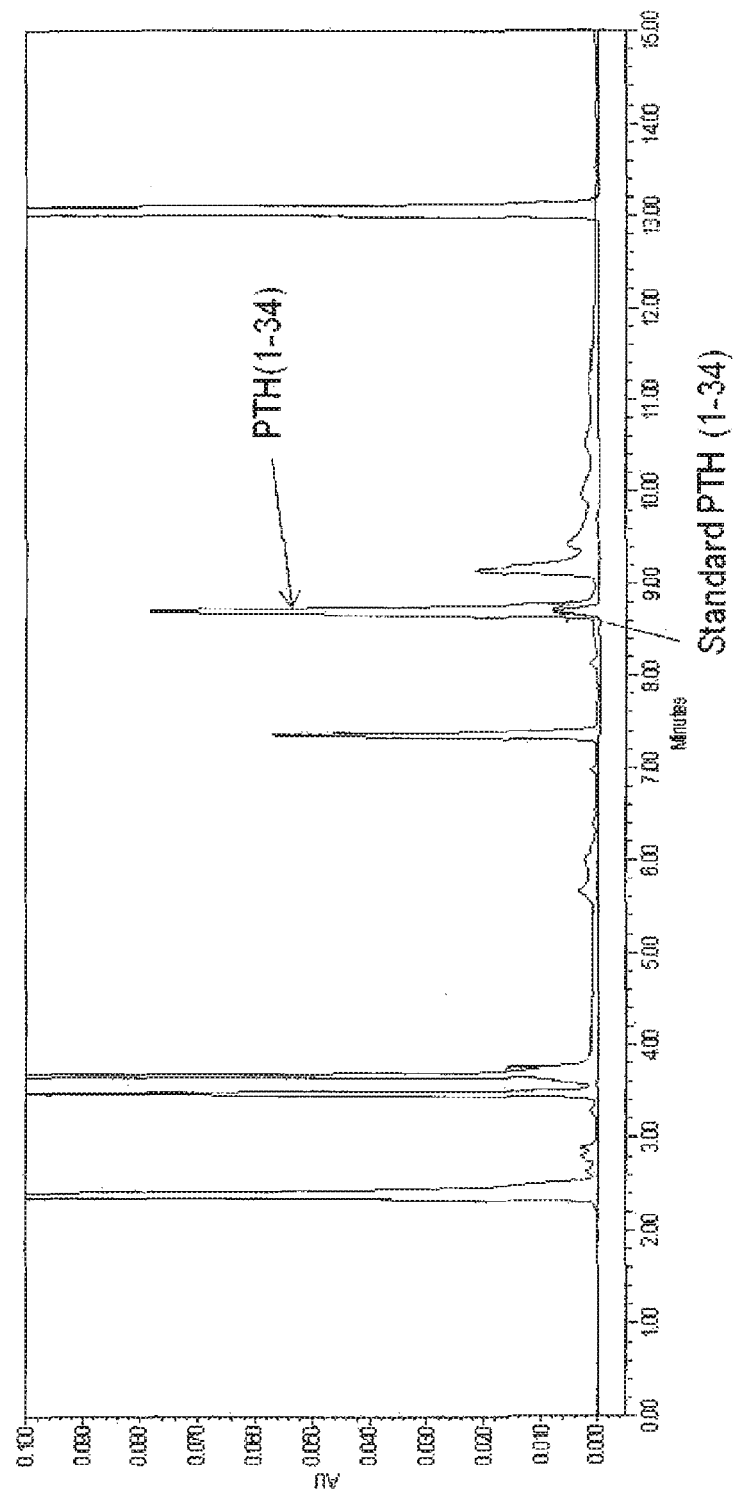

FIG. 9b presents a Tag PTH1 Fusion protein cleavage profile in RP-HPLC.

DETAILED DESCRIPTION

Before the present compositions and methods are described, it is to be understood that this invention is not limited to particular compounds, formulas or steps described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

As used herein and in the appended claims, the singular forms "a", "and", and "the" include plural referents unless the context clearly dictates otherwise. Thus, for example, reference to "a compound" includes a plurality of such compounds and reference to "the step" includes reference to one or more step and equivalents thereof known to those skilled in the art, and so forth. The term "or" is inclusive unless modified, for example, by "either." Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

In order to more clearly and concisely describe and point out the subject matter of the claimed invention, the following definitions are provided for specific terms which are used in the following written description:

"rhPTH" means recombinant human parathyroid hormone.

"Fusion protein" means protein created through the joining of two or more genes which originally coded for separate proteins.

"Fusion tag" means a short peptide, protein domain, or entire protein that can be fused to a target protein of interest to create a fusion protein.

"Cleavage site" means a region or site that cleaved by proteases or chemicals in a given protein sequence.

"TEV protease" is a site-specific cysteine protease that is found in and derived from the Tobacco Etch Virus (TEV).

Fusion tags have been used widely in heterologous expression systems as a technique to stabilize the recombinant product against proteolysis, increase the translational initiation efficiency or to serve as an affinity handle for the purification of the protein. A fusion tag is generally a protein or a peptide located either on the C- or N-terminal end of the target protein, which facilitates features such as improved solubility, detection, purification, localization or expression. Genetically engineered fusion tags allow the purification of virtually any protein without any prior knowledge of its biochemical properties. They can improve the variable yield and poor solubility of many recombinant proteins. Proper design and judicious use of the right fusion tag can enhance the solubility and promote proper folding of the protein of interest, leading to recovery of more functional protein. On the other hand, addition of fusion tags has been reported to result in changes in protein conformation, poor yields, loss or alteration of biological activity, and toxicity of the target protein. For these reasons, it is desirable to remove the tag from the target protein after expression by means of cleaving tags.

For example, PCT application WO 2011/151721 refers to construction of fusion partner comprising of 1-75 amino acids of truncated E. coli thioredoxin gene and a cleavage site, rhPTH gene wherein the fusion partner, thioredoxin gene is chosen, which is native protein to E. coli. Further, this publication relates to the fusion proteins of truncated thioredoxin to increase the production, activity, stability or solubility of recombinant heterologous proteins. The peptide or protein may be fused to the carboxyl terminus of the truncated thioredoxin molecule. The protein of interest includes PTH(1-34).

U.S. Patent Pub. No. 2010/0145033, refers to construction of a chimeric fusion protein comprising of a fusion partner consisting of 41 amino acids of E. coli β-galactosidase (LacZ) gene, an endopeptidase cleavage site, rhPTH gene fragment wherein the fusion partner, the (3-galactosidase gene is chosen being a protein native to E. coli, high percent GC content, corresponding peptide secondary structure, the secondary structure of ribonucleotide translating the same, and the fusion fragment as an aid facilitating downstream processing.

With specific reference to parathyroid hormone, Chinese patent CN1916172 refers to a method of preparing rhPTH (1-34) by use of expression vector capable of expressing fusion protein with an amino acid sequence from N- to C-terminal comprising thioredoxin, $His_6$, enterokinase recognition site, and parathyroid hormone 1-34 peptide. The publication also refers to purification of a recombinant fusion protein by nickel ion complexation affinity chromatography.

The present embodiments provide novel fusion tags for achieving high levels of expression of a protein of interest, particularly rhPTH(1-34). Various fusion tags were designed and created by recombining different sequence regions from different tags by using bioinformatics tools. In particular embodiments of the present invention, different fusion tag sequences with sizes ranging from 20-40 amino acids were designed using Expropriator data search to obtain higher expression levels and solubility of peptides/proteins. These fusion tags were used for the peptide rhPTH, cloned at the C-terminal end of the tag, to enable its use in production. A commercially available pET28a vector (Novagen) was used as the expression vector backbone. This vector was modified to bear a cassette comprising a His-tag fused with a novel tag followed by a TEV cleavage site and rhPTH. The novel expression vector was transformed into *E. coli* and expression of the chimeric fusion protein in fed batch fermentation was achieved.

The present embodiments provide fusion tags of 20 to 40 amino acids, the amino acid sequences of which are given in FIG. 1; tags homologous to these tags; or hybrid sequences (FIG. 1; Table 1). These sequences are evaluated using expropriator PROSO II software (available at on the internet) for solubility and expression stability in a bacterial system. See Smialowski et al., 279 FEBS J. 2192 (2012). Regarding the expropriator software, sequence-based PROtein SOlubility evaluator, the prediction is based on a classifier exploiting subtle differences between soluble proteins from TargetDB and the PDB and notoriously insoluble proteins from TargetDB. The method is based on around 80,000 proteins. Evaluated by 10-fold cross-validation it achieved accuracy=71%, area under ROC curve=0.785 and MCC (matthew's correlation coefficient)=0.422.

TABLE 1

Fusion tag peptides evaluated by PROSO II software

| SEQ ID NO | Predicted class | Size | Solubility score |
|---|---|---|---|
| NO: 1 | DSLRFLYDGIRIQADQAPEDLDMELGS | 27 | soluble; 0.948 |
| NO: 2 | GSDSEVNQEAKPEVKPEVKLGS | 22 | soluble; 0.954 |
| NO: 3 | GNQDEDFATVLVEEAKPEVKPEVKLGS | 27 | soluble; 0.887 |
| NO: 4 | EFTLTGLGQVIIGGGPAGLRTEEGFLVRGLFSHVVTEIL | 39 | soluble; 0.883 |
| NO: 5 | ENYPGFPEGISGPEAGREAKQAEKFGARIVMDEVQGEGS | 39 | soluble; 0.953 |
| NO: 6 | GKLTVAKLNIDQNPGTAPKYGIRGIPTTKVGALSKGQLGS | 40 | soluble; 0.950 |
| NO: 7 | MSDKIIHLTDDSFDTDVLKADGAILVDFWAEWGPKGS | 37 | insoluble; 0.237 | created using the amino acid sequences from FIG. 1. More specifically, particular embodiments of the present invention comprise tags selected from the group consisting of DSLRFLYDGIRIQADQAPEDLDMELGS (SEQ ID NO:1), GSDSEVNQEAKPEVKPEVKLGS (SEQ ID NO:2), GNQDEDFATVLVEEAKPEVKPEVKLGS (SEQ ID NO:3), EFTLTGLGQVIIGGGPAGLRTEEGFLVRGLFSHVVTEIL (SEQ ID NO:4), ENYPGFPEGISGPEAGREAKQAEKFGARIVMDEVQGEGS (SEQ ID NO:5), GKLTVAKLNIDQNPGTAPKYGIRGIPTTKVGALSKGQLGS (SEQ ID NO:6), MSDKIIHLTDDSFDTDVLKADGAILVDFWAEWGPKGS (SEQ ID NO:7), tags homologous to these tags, and hybrid sequences created using these sequences.

Embodiments of the present invention further provide for polynucleotides that encode the tags described herein. Embodiments of the present invention further provide for expression vector systems comprising polynucleotides encoding the fusion tags of the invention. In particular embodiments, the expression construct comprises the following components cloned in a vector backbone, starting from N-terminal end: a His-tag, a novel fusion tag, a TEV cleavage site, and rhPTH(1-34).

Further embodiments of the present invention provide processes of obtaining rhPTH via the fusion tags described herein, comprising: chemical synthesis of a polynucleotide encoding a fusion protein comprising the novel fusion tags and rhPTH; cloning of the fusion protein in vector backbone; expressing of fusion protein in *E. coli* cell in insoluble form; obtaining the rhPTH from the fusion protein, and partially purifying the rhPTH.

In the present invention, in order to optimize the solubility, short peptides were selected from the known soluble protein sequences. After in silico analysis, ten peptides containing 20-40 amino acid residues were selected as tags In other embodiments, the novel tag of the invention shares homology with a peptide of Table 1. "Homology", a "homologous peptide" or "homologous tag" refers to an amino acid sequence for which the primary sequence can be aligned with the peptide sequence (i.e., a tag initially identified in Table 1) using a conventional optimum alignment program such as GAP, BLOSUM, BLAST, BESTFIT or CLUSTAL software. The homology of one amino acid sequence with another amino acid sequence is defined as a percentage of identical amino acids in the two collated sequences. In particular, a sequence A will be considered to be homologous with a sequence B if said sequences A and B have at least 50%, at least 60%, at least 70%, at least 75%, at least 80%, at least 85%, or at least 90% identity after aligning the sequences using an optimum alignment program. Two amino acid sequences are also considered to be homologous if the sequences are quasi-identical, with the exception of a few residues that can represent 10% to 20% variability over the whole sequence. Further, amino acids with the same chemical function (such as Arg and Lys) are considered to be equivalent. More specifically, amino acid substitutions can be made conservatively; i.e., a substitute amino acid replaces an amino acid that has similar properties, such that one skilled in the art of peptide chemistry would expect the secondary structure and hydropathic nature of the homologous peptide to be substantially unchanged. In general, the following groups of amino acids represent conservative changes: (1) Ala, Pro, Gly, Glu, Asp, Gln, Asn, Ser, Thr; (2) Cys, Ser, Tyr, Thr; (3) Val, Ile, Leu, Met, Ala, Phe; (4) Lys, Arg, His; and (5) Phe, Tyr, Trp, His. Homologous tags within the scope of the invention may also, or alternatively, contain other modifications, including the deletion or addition of amino acids, that have minimal influence on the stimulatory properties, secondary structure and hydropathic nature of the fusion tag. Additionally, a homologous tag can be analyzed using PROSO II software regarding solubility. It should be noted, however, that these bioinformatics tools help in predicting the theoretical solubility and stability of different proteins/peptides, but in expression system other factors may affect the solubility of a given fusion construct. Thus, a homologous fusion tag can also be characterized for biological activity, i.e., function as a fusion tag in the production of rhPTH.

Regarding a fusion tag that is a hybrid tag created using sequences that include a portion of at least one of the tags of Table 1, note, for example, that the amino acid sequence EAKPEVKPEVKLGS (SEQ ID NO:8) is present in both Tag 2 and Tag 3. As such, these tags may be considered at least partial hybrids. These tags also share homology.

Another aspect of the present invention provides for a nucleic acid molecule or polynucleotide that encodes the novel fusion peptides described herein. Such polynucleotides can be designed based on the amino acid sequence of the tag and synthesized accordingly. For example, because of the degeneracy of the genetic code, a numerous DNA molecules can encode TagPTH1 (having amino acid sequence DSLRFLYDGIRIQADQAPEDLDMELGS (SEQ ID NO:1)), such that the DNA can be described by the following generic formula: GAYWSNYTNMGNT-TYYTNTAYGAYGGNATHMGNATHCARGCNGAY-CARGCNCCN GARGAYYTNGAYATGGARYTNGGN-WSN (SEQ ID NO:9), in which Y is C or T, W is T or A, S is C or G, N is A, T, C or G, M is C or A, H is T, C or A, and R is A or G.

TagPTH2, GSDSEVNQEAKPEVKPEVKLGS (SEQ ID NO:2) can be encoded by the DNA of formula: GGNWSN-GAYWSNGARGTNAAYCARGARGCNAARCCN-GARGTNAARCCNGARGTNA ARYTNGGNWSN (SEQ ID NO:10), in which N is A, T, C or G, Y is C or T, W is T or A, S is C or G, and R is A or G.

TagPTH3, GNQDEDFATVLVEEAKPEVKPEVKLGS (SEQ ID NO:3) can be encoded by the DNA sequence of the formula: GGNAAYCARGAYGARGAYTTYGCNACNGT-NYTNGTNGARGARGCNAARCCNGARG TNAARC-CNGARGTNAARYTNGGNWSN (SEQ ID NO:11), in which N is A, T, C or G, Y is C or T, R is A or G, W is T or A, and S is C or G.

TagPTH4, EFTLTGLGQVIIGGGPAGLRTEEGFLVR-GLFSHVVTEIL (SEQ ID NO:4), can be encoded by the DNA having the sequence represented by the formula: GARTTYACNYTNACNGGNYTNGGNCARGTNA-THATHGGNGGNGGNCCNGCNGGNY TNMGNACN-GARGARGGNTTYYTNGTNMGNGGNYTNTTYWSN-CAYGTNGTNACNGA RATHYTN (SEQ ID NO:12), in which Y is C or T, N is A, T, C or G, W is T or A, S is C or G, M is C or A, His T, C or A, and R is A or G.

TagPTH5, ENYPGFPEGISGPEAGREAKQAEKF-GARIVMDEVQGEGS (SEQ ID NO:5), can be encoded by the DNA sequence of the formula: GARAAYTAYCCNG-GNTTYCCNGARGGNATHWSNGGNCCNGARGCNG-GNMGNGAR GCNAARCARGCNGARAARTTYG-GNGCNMGNATHGTNATGGAYGARGTNCARGGNG ARGGNWSN (SEQ ID NO:13), in which N is A, T, C or G, R is A or G, H is T, C or A, Y is C or T, M is C or A, W is T or A, and S is C or G.

TagPTH6, GKLTVAKLNIDQNPGTAPKYGIRGIPTTK-VGALSKGQLGS (SEQ ID NO:6), can be encoded by the DNA sequence of the formula: GGNAARYT-NACNGTNGCNAARYTNAAYATHGAYCARAAYC-CNGGNACNGCNCCNA ARTAYGGNATHMGNGG-NATHCCNACNACNAARGTNGGNGCNYTNWSNAA-RGGNC ARYTNGGNWSN (SEQ ID NO:14), in which N is A, T, C or G, R is A or G, H is T, C or A, Y is C or T, M is C or A, W is T or A, and S is C or G.

Tag PTH7, MSDKIIHLTDDSFDTDVLKADGAILVDF-WAEWGPKGS (SEQ ID NO:7) can be encoded by a DNA represented by the generic formula ATGWSN-GAYAARATHATHCAYYTNACNGAYGAYWSNTTY-GAYACNGAYGTNYTNA ARGCNGAYGGNGC-NATHYTNGTNGAYTTYTGGGCNGARTGGGGNCC-NAARGGNWS N (SEQ ID NO:15), in which Y is C or T, W is T or A, S is C or G, N is A, T, C or G, M is C or A, H is T, C or A, and R is A or G.

Such polynucleotides can further be optimized for expression in *E. coli*. Following at least partial artificial synthesis, the polynucleotide molecules can be manipulated by PCR and cloning techniques which are well-known in the art. Moreover, the present embodiments provide for polynucleotides that encode homologous tags and tags comprised of portions of the particular tags described herein.

The novel fusion tags of the invention were used for expression of the peptide rhPTH cloned at the C-terminal end of the tag to enable its use in the production. A commercially available pET28a vector (Novagen) was used as vector backbone, providing T7 promoter-driven expression of the recombinant protein. This vector was modified to bear a cassette comprising of His-tag fused with the novel tag followed by TEV cleavage site and rhPTH. Other tags and cleavage sites known in the art can also be placed in the genetic construct comprising the fusion tags of the present invention by techniques well-known in the art. This new expression vector was transformed into *E. coli* and expression of the chimeric fusion protein in fed batch fermentation was achieved. Other expression vectors and host cell systems can be utilized based on the teachings of this specification without undue experimentation.

EXAMPLES

Example 1

Construction of Fusion Proteins with the Novel Fusion Tag Sequences

Figure 3:
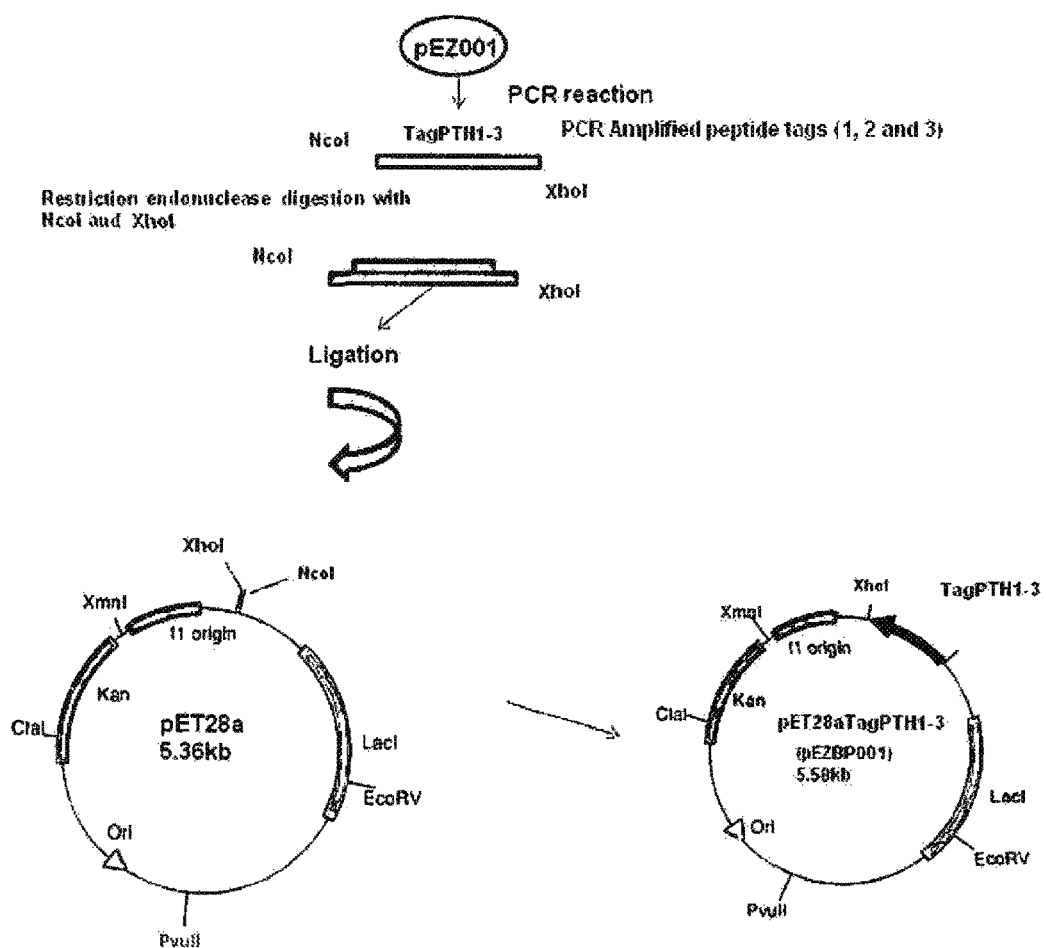
FIG. 3 shows a schematic for construction of example plasmids (pET28a TagPTH (1-3)).

The fusion tags given in Table 1 were used to create fusion proteins using rhPTH as the expression target, and synthesized along with His-tag and TEV cleavage site (FIG. 2). The construction process is exemplified in FIG. 3, and such methods are well-known in the person skilled in the art. These novel tags were separately attached to the N-terminal end of rhPTH which was taken as the expression target. A TEV cleavage site was also included between the rhPTH and the novel tags to enable separation of the tag from the rhPTH. To ease purification, a $His_6$ tag was included at the N-terminal end of the novel tags. Initiation and termination codons were also included at N-terminal and C-terminal side of the fusion peptide respectively.

Example 2

Construction of Thiredoxin (Trx) PTH Fusion Protein

To compare expression levels and yield of protein/peptide of interest using the novel fusion tags described herein, a different tag (Trx) of size 100 amino acids was used along with PTH. The Trx tag was amplified and cloned into pET28a vector and then rhPTH amplified along with TEV protease and cloned into pET28aTrx.

Example 3

Cloning and Expression of TagPTH1; Amplification and Cloning of Tag 1 (DSLRFLYDGIRIQADQAPEDLDMELGS (SEQ ID NO:1) with PTH TagPTH1 gene was amplified using synthetic DNA as template and was cloned in to pET28a at NcoI/XhoI sites. Primers were designed in such a way that the amplified product contains amino acids of TagPTH1. Primers used for PCR amplification were forward primer: AGCTATCCATGGGCCACCACCACCACCATCAC (SEQ ID NO:16); reverse primer: AGCTCTCTCGAGTTAAAAATTATGCACATCCTGCAG (SEQ ID NO:17)

Regarding PCR conditions, PTH(1-34) gene along with novel Tag 1 were PCR-amplified using Pfu DNA polymerase with the following amplification conditions. Initial denaturation of 4 min at 94° C. followed by 30 cycles of 94° C. for 30 sec, and 72° C. for 30 sec, with annealing temperature of 58° C. for 30 sec. After a final extension of 5 min at 72° C., the PCR amplified products were checked on 2% agarose gel (FIG. 4), purified and then digested with NcoI/XhoI and ligated to the pET-28a vector at the similar sites. The ligation mix was used to transform competent TOP10 cell line and the from the resultant 5-10 colonies were inoculated in 5-10 ml LB for overnight incubation in shaker for 12-16 hr. Plasmid DNA was isolated from the cultures and restriction analysis was done to confirm the release of insert by NcoI/XhoI digestion. The resultant clones were designated as pET-TEVPTHa

Example 4

Cloning and Expression of TagPTH2; Amplification and Cloning of Tag 2 (GSDSEVNQEAKPEVKPEVKLGS) (SEQ ID NO:2) Along with PTH The TagPTH2 gene was amplified using a synthetic DNA as template and was cloned in to pET28a at NcoI/XhoI sites. Primers were designed in such a way that the amplified product contains amino acids of TagPTH2. Primers for PCR amplification: forward: AGCTATCCATGGGCCACCACCACCACCATCAC (SEQ ID NO:18); reverse: AGCTCTCTCGAGTTAAAAATTATGCACATCCTGCAG (SEQ ID NO:19).

Regarding the PCR conditions, PTH(1-34) gene along with Tag 2 were PCR-amplified using Pfu DNA polymerase with the following amplification conditions. Initial denaturation of 4 min at 94° C. followed by 30 cycles of 94° C. for 30 sec, and 72° C. for 30 sec, with annealing temperature of 58° C. for 30 sec. After a final extension of 5 min at 72° C., the PCR amplified products were checked on 2% agarose gel (FIG. 4), purified, and then digested with NcoI/XhoI and ligated to the pET-28a vector at the similar sites. The ligation mix was used to transform competent TOP10 cell line and the from the resultant 5-10 colonies were inoculated in 5-10 ml LB for overnight incubation in shaker for 12-16 hr. Plasmid DNA was isolated from the cultures and restriction analysis was done to confirm the release of insert by NcoI/XhoI digestion. The resultant clones were designated as pET-TEVPTHb.

Example 5

Cloning and Expression of TagPTH3; Amplification and Cloning of Tag 3 (GNQDEDFATVLVEEAKPEVKPEVKLGS) (SEQ ID NO:3) Along with PTH The TagPTH3 gene was amplified using synthetic DNA as template and was cloned in to pET28a at NcoI/XhoI sites. Primers were designed in such a way that the amplified product contains amino acids of TagPTH3. Primers for PCR amplification were forward: AGCTATCCATGGGCCACCACCACCACCATCAC (SEQ ID NO:20); reverse: AGCTCTCTCGAGTTAAAAATTATGCACATCCTGCAG (SEQ ID NO:21).

Regarding the PCR conditions, the PTH(1-34) gene along with Tag 3 were PCR-amplified using Pfu DNA polymerase with the following amplification conditions. Initial denaturation of 4 min at 94° C. followed by 30 cycles of 94° C. for 30 sec, and 72° C. for 30 sec, with annealing temperature of 58° C. for 30 sec. After a final extension of 5 min at 72° C., the PCR amplified products were checked on 2% agarose gel (FIG. 4), purified, and then digested with NcoI/XhoI and ligated to the pET-28a vector at the similar sites. The ligation mix was used to transform competent TOP10 cell line and the from the resultant 5-10 colonies were inoculated in 5-10 ml LB for overnight incubation in shaker for 12-16 hr. Plasmid DNA was isolated from the cultures and restriction analysis was done to confirm the release of insert by NcoI/XhoI digestion. The resultant clones were designated as pET-TEVPTHc.

Example 6

Fusion Protein Expression

The restriction positive recombinant plasmids encoding the TagPTH (1-3) constructs were transformed into *E. coli* BL21DE3 for expression analysis. Single colonies were inoculated to 5-10 ml LB/kanamycin media allowed for growing at 30-37° C. till OD of 0.6-1.0, and the cultures induced with 250 µM-1 mM IPTG for 3-5 hrs. The samples were analyzed for the expression on 15% SDS PAGE gels. (FIG. 5). Based on the expression profiles among the three fusion constructs, pET-TagPTH1 was seen to have better expression data and hence was studied further.

Example 7

Cloning of Trx Gene to Obtain pET28aTrx; Amplification and Cloning of Trx Gene into pET28a The Trx gene was amplified using pET 32a plasmid DNA as template and was cloned in to pET28a at NdeI/BamHI sites. Primers were designed in such a way that the amplified product contains amino acids of Trx. Primers for PCR amplification were forward: AGCTATCATATGAGCGATAAAATTATTCAC (SEQ ID NO:22); reverse: TATCGAGGATCCGTTAGCGTCGAGGAACTC (SEQ ID NO:23).

Regarding the PCR conditions, the Trx gene was PCR-amplified using Pfu DNA polymerase with the following amplification conditions. Initial denaturation of 4 min at 94° C. followed by 30 cycles of 94° C. for 30 sec, and 72° C. for 30 sec, with annealing temperature of 58° C. for 30 sec. After a final extension of 5 min at 72° C., the PCR amplified products were checked on 2% agarose gel purified, and then digested with NdeI/BamHI and ligated to the pET-28a vector at the similar sites. The ligation mix was used to transform competent TOP10 cell line and from the resultant 5-10 colonies were inoculated in 5-10 ml LB for overnight incubation in shaker for 12-16 hr. Plasmid DNA was isolated from the cultures and restriction analysis was done to confirm the release of insert by XbaI/BamHI digestion. The resultant clones were designated as pET-Trx.

Example 8

Cloning of PTH Gene into pET28aTrx and Expression; Amplification and Cloning of PTH into pET-Trx Along with TEV Protease Site The PTH gene was amplified using synthetic DNA as template along with TEV protease cleavage site and was cloned in to pET28aTrx at BamHI/XhoI sites. Primers were designed in such a way that the amplified product contains amino acids of PTH. Primers for PCR amplification were forward: TATAGAGGATCCGAAAACCTGTATTTTCA-GAGC (SEQ ID NO:24); reverse: AGCTCTCTCGAGT-TAAAAATTATGCACATCCTGCAG (SEQ ID NO:25).

Regarding the PCR conditions, the Trx gene was PCR-amplified using Pfu DNA polymerase with the following amplification conditions. Initial denaturation of 4 min at 94° C. followed by 30 cycles of 94° C. for 30 sec, and 72° C. for 30 sec, with annealing temperature of 58° C. for 30 sec. After a final extension of 5 min at 72° C., the PCR amplified products were checked on 2% agarose gel purified, and then digested with BamH/XhoI and ligated to the pET-28a Trx vector at the similar sites. The ligation mix was used to transform competent TOP10 cell line and from the resultant 5-10 colonies were inoculated in 5-10 ml LB for overnight incubation in shaker for 12-16 hr. Plasmid DNA was isolated from the cultures and restriction analysis was done to confirm the release of insert by XbaI/BamHI digestion. The resultant clones were designated as pET-TrxPTH Example 9

Fusion Protein Expression

The restriction positive recombinant plasmids encoding the TrxPTH were transformed into *E. coli* BL21DE3 for expression analysis. Single colonies were inoculated into 5-10 ml LB/Kanamycin media allowed to grow at 30-37° C. until the culture reached an OD of 0.6-1.0, and the cultures were induced with 250 µM-1 mM IPTG for 3-5 hrs and checked for expression.

Example 10

Shake Flask Studies

*E. coli* BL21 (DE3) cells carrying pET Trx-PTH and TagPTH1 were grown in large scale (1 L) at 37° C., induced with 250 µM IPTG and allowed to grow overnight. These induced cultures (0.2O.D cells) were analyzed for expression on 15% SDS PAGE (FIG. 6). After expression analysis, these cultures were harvested by centrifugation at >4000 rpm for >10 min. The cells were resuspended in 100 ml of 50 mM Tris-HCl (pH 8.0) and lysed by sonication. The cell lysates were centrifuged at >7000 rpm for >15 minutes in cold and the soluble and the insoluble proteins were collected separately. The prediction using bioinformatics tools was to achieve soluble protein; in practice, however, the TagPTH1 was obtained in the insoluble fraction. This could be due to various biological factors, such as the very high expression level pushing protein into insoluble bodies.

The above insoluble fractions containing the fusion proteins were taken for TEV protease digestion. The fractions were resuspended in equal volume of 1-8 M urea pH 7.0-pH 9.0. Aliquots of 5-10 ml of these samples were diluted to 50-100 ml and incubated with 5-20 U of TEV protease enzyme in the presence of 20-100 mM Tris and 0.5-2 mM EDTA. The reactions were incubated at 30° C. for 1-5 hrs, and analyzed on RP-HPLC (FIG. 7) for digestion. The total amount of PTH(1-34) obtained after protease digestion in case of TagPTH1 was two- to five-fold higher than the yield observed for pET Trx-PTH (FIG. 7).

Example 11

Fermentation, Isolation of Fusion Protein, and TEV Protease Digestion

The recombinant *E. coli* carrying restriction positive recombinant plasmid TagPTH1, that had exhibited suitable peptide yield following expression in small-scale culture, was used in larger-scale production fermentation as follows: The initial inoculum was cultured before it was inoculated into the fermentation medium. Fermentation was carried out in a fed batch mode using yeast extract, tryptone medium comprised of salts like potassium phosphate and ammonium phosphate. Glucose, mannitol, sorbitol or glycerol was used as the source of carbon and energy. Fermentation process parameters followed were that of typical *E. coli* fermentation process, i.e., pH 6.0 to pH 8.0, temperature 27° C. to 40° C., aeration 0.1 to 3 vvm, etc., as known in the art. Nutrient feed medium was composed of yeast extract, tryptone, potassium and ammonium phosphate salts and glucose, mannitol, sorbitol or glycerol. The feed strategy adopted was a "linear feed strategy." The feed strategy helped to keep the acetate formation below 4 g/L during the entire batch. IPTG was used as the inducer at a concentration ranging from 0.05 mM to 2 mM. The fermentation batch time was 10-18 hr, and cell density achieved was OD (600 nm) 110. Growth inhibition was not observed at different concentrations of inducer, which helped to achieve higher biomass along with expression of the target protein.

The fermentation broth was harvested and centrifuged at >4000 rpm at 4° C. for 5-15 min and spent medium was collected separately. The induced cell pellet was processed for disruption by suspending in 10 mM TrisCl, pH 7.5-8.5 at an OD(600)>50, after which the suspension was passed through a cell homogenizer such that the turbidity of the solution after homogenization was reduced by at least 80%, which was indicative of bacterial cell lysis. The entire process was carried out in cold by keeping the cell suspension as well as the cell lysis reaction on ice. The homogenizer was also connected to chilled water line as an alternative.

The cell lysate was centrifuged at >7000 rpm for >15 minutes in cold and the soluble and the insoluble proteins were collected separately. The insoluble fraction contained the TEV-PTH(1-34) and was stored for further downstream process.

The crude insoluble fraction was used for digestion with TEV protease. The fraction was suspended in 1-8 M urea pH 7.0-pH 9.0, 1-5 ml of these sample diluted to 10-50 ml was incubated with 0.5-5 U of TEV protease enzyme with 20-100 mM Tris buffer and 0.5-1.5 mM EDTA. The reaction mix was incubated at 30° C. for 1-5 hr. After digestion of fusion protein, the samples were analyzed on SDS PAGE (FIG. 8) and on RP-HPLC (FIGS. 9a and 9b). PTH(1-34) was released after TEV protease digestion as seen FIG. 8, lane 2. The digested sample was then partially purified using affinity column chromatography and PD-10 protein desalting column.

Alternatively, the fed batch fermentation is followed by a two-step purification processes comprising Ni-NTA/ Ultrafiltration•chromatography followed by preparative RP-HPLC to yield a target protein of >99% purity. The present invention results in a simple, cost-effective, environmentally benign process of producing high purity rhPTH(1-34).

The invention claimed is:

1. A recombinant fusion tag of 20-40 amino acid for expression and purification of recombinant human parathyroid hormone (rhPTH), said fusion tag comprising an amino acid sequence selected from the group consisting of:
   (a) the amino acid sequence set forth in SEQ ID NO.1;
   (b) the amino acid sequence set forth in SEQ ID NO.2;
   (c) the amino acid sequence set forth in SEQ ID NO.3;
   (d) the amino acid sequence set forth in SEQ ID NO.4;
   (e) the amino acid sequence set forth in SEQ ID NO.5;
   (f) the amino acid sequence set forth in SEQ ID NO.6; and
   (g) the amino acid sequence set forth in SEQ ID NO.7.

2. A polynucleotide encoding the recombinant fusion tag of claim 1.

3. A recombinant vector comprising the polynucleotide of claim 2.

4. An expression vector comprising the polynucleotide of claim 2.

5. The expression vector of claim 4, wherein the vector includes a pET28a vector backbone.

6. The expression vector of claim 4, wherein the fusion tag is fused with a His-tag, followed by a TEV cleavage site and rhPTH.

7. The recombinant fusion tag of claim 1, wherein the tag comprises the amino acid sequence set forth in SEQ ID NO:1.

8. The recombinant fusion tag of claim 1, wherein the tag comprises the amino acid sequence set forth in SEQ ID NO:2.

9. The recombinant fusion tag of claim 1, wherein the tag comprises the amino acid sequence set forth in SEQ ID NO:3.

10. The recombinant fusion tag of claim 1, wherein the tag comprises the amino acid sequence set forth in SEQ ID NO:4.

11. The recombinant fusion tag of claim 1, wherein the tag comprises the amino acid sequence set forth in SEQ ID NO:5.

12. The recombinant fusion tag of claim 1, wherein the tag comprises the amino acid sequence set forth in SEQ ID NO:6.

13. The recombinant fusion tag of claim 1, wherein the tag comprises the amino acid sequence set forth in SEQ ID NO:7.

14. A process for obtaining recombinant human parathyroid hormone (rhPTH), said process comprising:
   (a) synthesizing a DNA that encodes a fusion tags of 20-40 amino acid of claim 1;
   (b) preparing a genetic construct that encodes a fusion protein comprising the fusion tag of step (a) and rhPTH;
   (c) cloning the construct of step (a) into an expression vector;
   (d) expressing the fusion protein in *E. coli*;
   (e) obtaining the rhPTH from the fusion protein; and
   (f) partially purifying the rhPTH.

* * * * *

SEQUENCE LISTING

<160> NUMBER OF SEQ ID NOS: 7

<210> SEQ ID NO 1
<211> LENGTH: 27
<212> TYPE: PRT
<213> ORGANISM: Escherichia coli

<400> SEQUENCE: 1

Asp Ser Leu Arg Phe Leu Tyr Asp Gly Ile Arg Ile Gln Ala Asp Gln
1               5                   10                  15

Ala Pro Glu Asp Leu Asp Met Glu Leu Gly Ser
            20                  25

<210> SEQ ID NO 2
<211> LENGTH: 22
<212> TYPE: PRT
<213> ORGANISM: Escherichia coli

<400> SEQUENCE: 2

Gly Ser Asp Ser Glu Val Asn Gln Glu Ala Lys Pro Glu Val Lys Pro
1               5                   10                  15

Glu Val Lys Leu Gly Ser
            20

<210> SEQ ID NO 3
<211> LENGTH: 27
<212> TYPE: PRT
<213> ORGANISM: Escherichia coli

<400> SEQUENCE: 3

Gly Asn Gln Asp Glu Asp Phe Ala Thr Val Leu Val Glu Glu Ala Lys
1               5                   10                  15

Pro Glu Val Lys Pro Glu Val Lys Leu Gly Ser
            20                  25

<210> SEQ ID NO 4
<211> LENGTH: 39
<212> TYPE: PRT
<213> ORGANISM: Escherichia coli

<400> SEQUENCE: 4

Glu Phe Thr Leu Thr Gly Leu Gly Gln Val Ile Ile Gly Gly Gly Pro
1               5                   10                  15

Ala Gly Leu Arg Thr Glu Glu Gly Phe Leu Val Arg Gly Leu Phe Ser
            20                  25                  30

His Val Val Thr Glu Ile Leu
        35

<210> SEQ ID NO 5
<211> LENGTH: 39
<212> TYPE: PRT
<213> ORGANISM: Escherichia coli

<400> SEQUENCE: 5

Glu Asn Tyr Pro Gly Phe Pro Glu Gly Ile Ser Gly Pro Glu Ala Gly

-continued

```
                1               5                      10                          15
Arg Glu Ala Lys Gln Ala Glu Lys Phe Gly Ala Arg Ile Val Met Asp
                        20                      25                      30

Glu Val Gln Gly Glu Gly Ser
                35

<210> SEQ ID NO 6
<211> LENGTH: 40
<212> TYPE: PRT
<213> ORGANISM: Escherichia coli

<400> SEQUENCE: 6

Gly Lys Leu Thr Val Ala Lys Leu Asn Ile Asp Gln Asn Pro Gly Thr
1               5                      10                          15

Ala Pro Lys Tyr Gly Ile Arg Gly Ile Pro Thr Thr Lys Val Gly Ala
                        20                      25                      30

Leu Ser Lys Gly Gln Leu Gly Ser
                35                      40

<210> SEQ ID NO 7
<211> LENGTH: 37
<212> TYPE: PRT
<213> ORGANISM: Escherichia coli

<400> SEQUENCE: 7

Met Ser Asp Lys Ile Ile His Leu Thr Asp Asp Ser Phe Asp Thr Asp
1               5                      10                          15

Val Leu Lys Ala Asp Gly Ala Ile Leu Val Asp Phe Trp Ala Glu Trp
                        20                      25                      30

Gly Pro Lys Gly Ser
                35
```